(12) United States Patent
Vitaris et al.

(10) Patent No.: US 8,795,237 B2
(45) Date of Patent: Aug. 5, 2014

(54) TRANSPARENT CATHETER SECUREMENT SYSTEM

(75) Inventors: Ronald F. Vitaris, Worcester, MA (US); Anthony Trupiano, Lakeville, MA (US); Steven D. King, Bridgewater, NY (US); Brian Dowd, Dedham, MA (US); David Parsons, Mansfield, MA (US)

(73) Assignee: Covidien LP, Mansfield, MA (US)

( * ) Notice: Subject to any disclaimer, the term of this patent is extended or adjusted under 35 U.S.C. 154(b) by 276 days.

(21) Appl. No.: 12/568,789

(22) Filed: Sep. 29, 2009

(65) Prior Publication Data

US 2010/0106095 A1    Apr. 29, 2010

Related U.S. Application Data

(60) Provisional application No. 61/101,208, filed on Sep. 30, 2008.

(51) Int. Cl.
*A61M 5/32* (2006.01)

(52) U.S. Cl.
USPC .......................................................... 604/179

(58) Field of Classification Search
USPC ................................................. 604/174–180
See application file for complete search history.

(56) References Cited

U.S. PATENT DOCUMENTS

| | | |
|---|---|---|
| 4,224,937 A | 9/1980 | Gordon |
| 4,250,880 A | 2/1981 | Gordon |
| 4,397,647 A | 8/1983 | Gordon |
| 4,449,975 A | 5/1984 | Perry |
| 4,460,356 A | 7/1984 | Moseley |
| 4,490,141 A | 12/1984 | Lacko et al. |
| 4,527,559 A * | 7/1985 | Roxburg et al. ......... 128/207.17 |
| 4,563,177 A | 1/1986 | Kamen |
| 4,698,057 A | 10/1987 | Joishy |
| 4,737,143 A | 4/1988 | Russell |
| 4,826,486 A | 5/1989 | Palsrok |
| 4,863,432 A | 9/1989 | Kvalo |
| 4,898,587 A * | 2/1990 | Mera ............................ 604/174 |
| 4,976,698 A | 12/1990 | Stokley |
| 5,084,026 A | 1/1992 | Shapiro |
| 5,215,532 A | 6/1993 | Atkinson |

(Continued)

FOREIGN PATENT DOCUMENTS

| | | |
|---|---|---|
| EP | 1 719 537 A2 | 11/2006 |
| GB | 1 465 682 A | 2/1977 |

(Continued)

OTHER PUBLICATIONS

Written Opinion and International Search Report from counterpart International Application No. PCT/US2009/058909 filed Sep. 30, 2009.

(Continued)

*Primary Examiner* — Aarti B Berdichevsky
*Assistant Examiner* — Bradley Osinski

(57) ABSTRACT

A securement device for securing a catheter to a patient is provided. The securement device includes a proximal portion having a pliable support and at least one securement arm extending away from the pliable support. The pliable support defines a slot configured to receive at least a portion of a catheter. A distal portion of the securement device includes an adhesive surface configured to be folded over the proximal portion to secure the proximal portion to a patient.

22 Claims, 4 Drawing Sheets

(56) References Cited

U.S. PATENT DOCUMENTS

| | | | |
|---|---|---|---|
| 5,300,037 A | 4/1994 | Delk et al. | |
| 5,306,256 A * | 4/1994 | Jose | 604/180 |
| 5,314,411 A | 5/1994 | Bierman et al. | |
| 5,344,415 A | 9/1994 | DeBusk | |
| 5,354,282 A | 10/1994 | Bierman | |
| 5,372,589 A | 12/1994 | Davis | |
| 5,380,294 A | 1/1995 | Persson | |
| 5,413,562 A | 5/1995 | Swauger | |
| 5,685,859 A * | 11/1997 | Kornerup | 604/180 |
| 5,810,781 A | 9/1998 | Bierman | |
| 5,833,667 A | 11/1998 | Bierman | |
| 5,897,519 A | 4/1999 | Shesol et al. | |
| 5,947,931 A | 9/1999 | Bierman | |
| 6,113,577 A | 9/2000 | Hakky et al. | |
| 6,231,548 B1 | 5/2001 | Bassett | |
| 6,273,873 B1 * | 8/2001 | Fleischer | 604/174 |
| 6,290,676 B1 | 9/2001 | Bierman | |
| 6,302,867 B1 | 10/2001 | Brown, Jr. et al. | |
| 6,311,933 B1 | 11/2001 | Starchevich | |
| 6,428,515 B1 | 8/2002 | Bierman et al. | |
| 6,582,403 B1 | 6/2003 | Bierman et al. | |
| 6,673,046 B2 | 1/2004 | Bierman et al. | |
| 7,014,627 B2 | 3/2006 | Bierman | |
| 7,018,362 B2 | 3/2006 | Bierman et al. | |
| 7,119,247 B2 | 10/2006 | Worthley | |
| 7,153,291 B2 | 12/2006 | Bierman | |
| 7,220,246 B2 | 5/2007 | Raulerson et al. | |
| D547,862 S | 7/2007 | Dikeman et al. | |
| 7,413,561 B2 | 8/2008 | Raulerson et al. | |
| 2002/0188255 A1 | 12/2002 | Bierman et al. | |
| 2005/0027258 A1 | 2/2005 | Bierman et al. | |
| 2006/0129103 A1 | 6/2006 | Bierman et al. | |
| 2008/0065022 A1 | 3/2008 | Kyvik et al. | |
| 2008/0097334 A1 | 4/2008 | Dikeman et al. | |
| 2008/0171993 A1 | 7/2008 | Beran | |
| 2008/0200880 A1 | 8/2008 | Kyvik et al. | |
| 2009/0093769 A1 | 4/2009 | Wright et al. | |

FOREIGN PATENT DOCUMENTS

| | | |
|---|---|---|
| WO | WO 92/12757 | 8/1992 |
| WO | WO 98/10823 | 3/1998 |
| WO | WO 98/10823 A1 | 3/1998 |
| WO | WO 98/15312 A1 | 4/1998 |
| WO | WO 99/55410 A1 | 11/1999 |

OTHER PUBLICATIONS

Extended European Search Report dated Feb. 21, 2012 from corresponding EP Application No. 09818392.4; (7 pages).

European Examination Report dated Sep. 23, 2013 in European Application No. 09 818 392.

Rejection Decision dated Sep. 5, 2013 in Chinese Patent Application No. 200980138326.

* cited by examiner

TRANSPARENT CATHETER SECUREMENT SYSTEM

CROSS-REFERENCE TO RELATED APPLICATION

The present application claims benefit to and priority from U.S. Provisional Application No. 61/101,208, filed Sep. 30, 2008, the entire content of which is incorporated herein by reference.

BACKGROUND

1. Technical Field

This present disclosure relates to a securement system for securing a catheter to a patient. More particularly, the present disclosure relates to a transparent securement system for securely supporting a catheter to a patient and protecting a catheterization site.

2. Background of Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line may be secured to the patient in a variety of ways. Most commonly, this involves taping the catheter or medical line to the patient. Additionally, a transparent dressing is applied over a portion of the catheter or medical line to protect the catheterization site while enabling visualization.

Securing a catheter with tape upon the patient traditionally is cumbersome and has certain drawbacks. The use of tape at the insertion site can retain dirt or other contaminant particles, potentially leading to infection of the patient. Tape also fails to limit catheter motion and, therefore, contributes to motion related complications like phlebitis, infiltration, and catheter migration. Additionally, removal of the tape can itself cause undesired motion of the catheter upon the patient.

Tape and transparent dressings also require periodic changes. The frequent, often daily, removal and reapplication of adhesive tape to the skin of the patient may excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue may also make the catheter or medical line stickier and more difficult to handle for healthcare providers.

Accordingly, a need exists for an efficient system for securing a catheter to a patient that enables a clinician to monitor the catheter and catheter insertion site for infection, irritation and other associated complications.

SUMMARY

A securement device for securing a catheter to a patient is provided. The securement device includes a proximal portion having a foam support and at least one securement arm extending away from the pliable support. The pliable support defines a slot configured to receive at least a portion of a catheter. A distal portion of the securement device includes an adhesive surface configured to be folded over the proximal portion to secure the proximal portion to a patient.

The at least one securement arm may include an adhesive surface. The adhesive surfaces may be protected by release layers. The distal portion of the securement device may be transparent. The distal portion may define a substantially rectangular member. The proximal portion may include two securement arms. The proximal portion may also include an adhesive portion on a bottom surface thereof.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the present disclosure will be shown with respect to catheter 5 (FIG. 2) having a cannula 5a and a hub 5b. Catheter 5 will be shown attached to a tube set 6. Catheter 5 and tube set 6 are shown for illustrative purposes only. The aspects of the present disclosure should not be read as limited by catheter 5 and/or tube set 6.

Figure 1A:
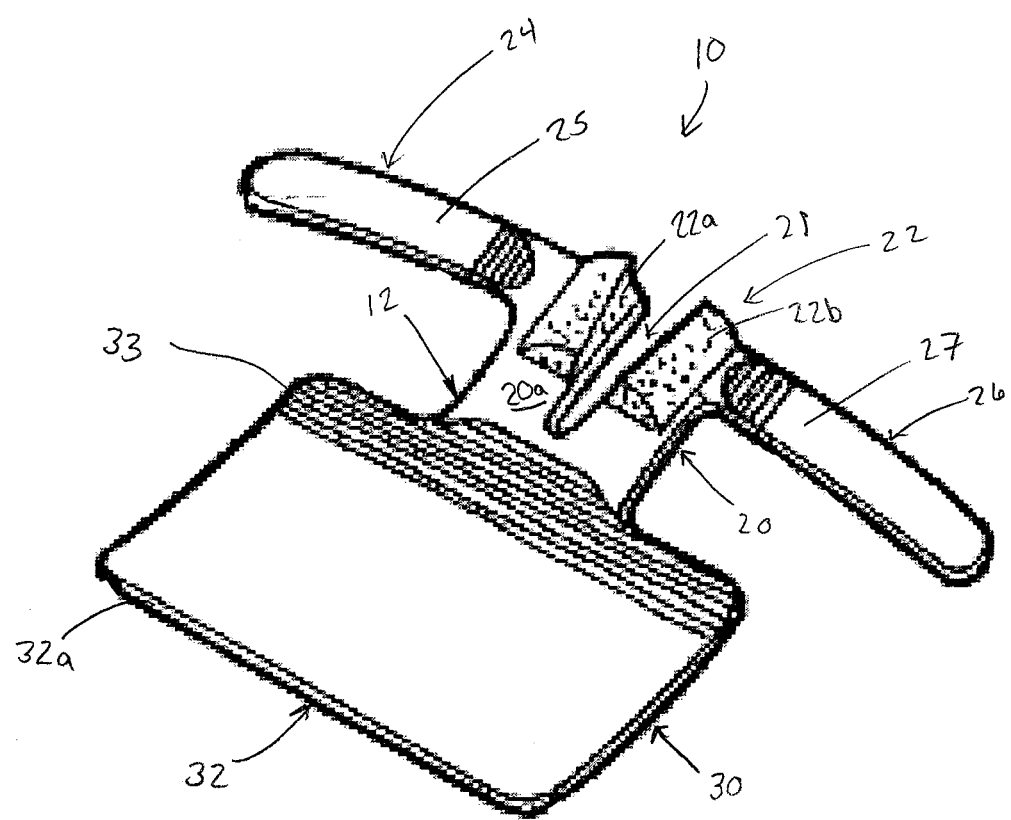
FIG. 1A is a perspective top view of an embodiment of the securement device of the present disclosure.
Figure 1B:
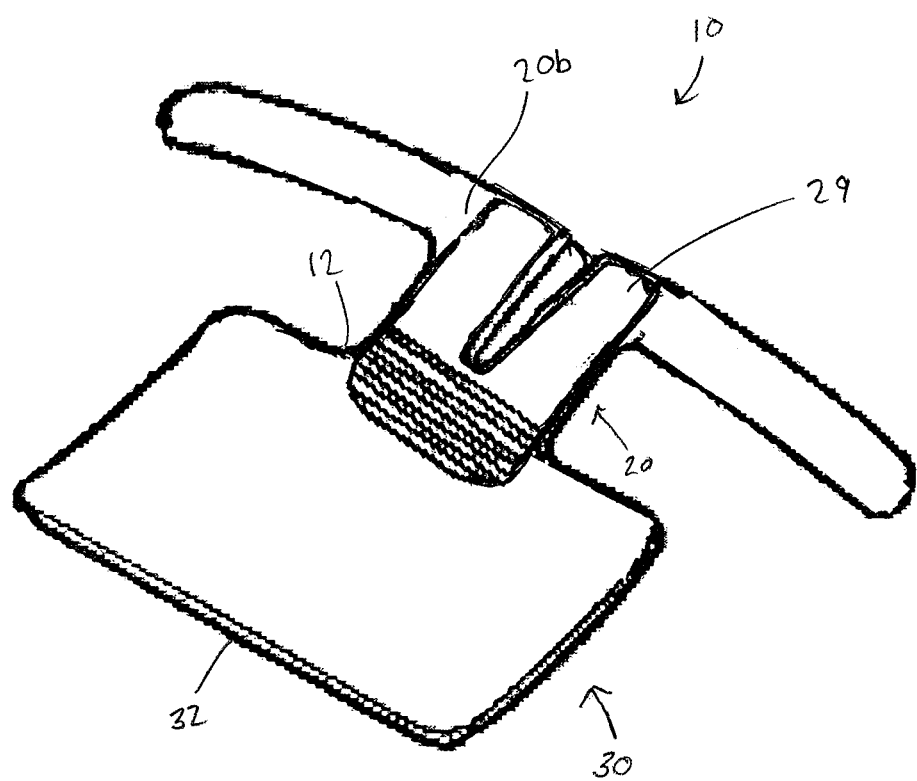
FIG. 1B is a perspective bottom view of the securement device of FIG. 1A.

With reference now to FIGS. 1A and 1B, a securement device according to the present disclosure is shown generally as securement device 10. Securement device 10 includes a transparent base 12 having a slotted proximal portion 20 and a substantially rectangular distal portion 30. Transparent base 12 may be constructed of a clear flexible plastic or other suitable polymeric material.

Figure 2:
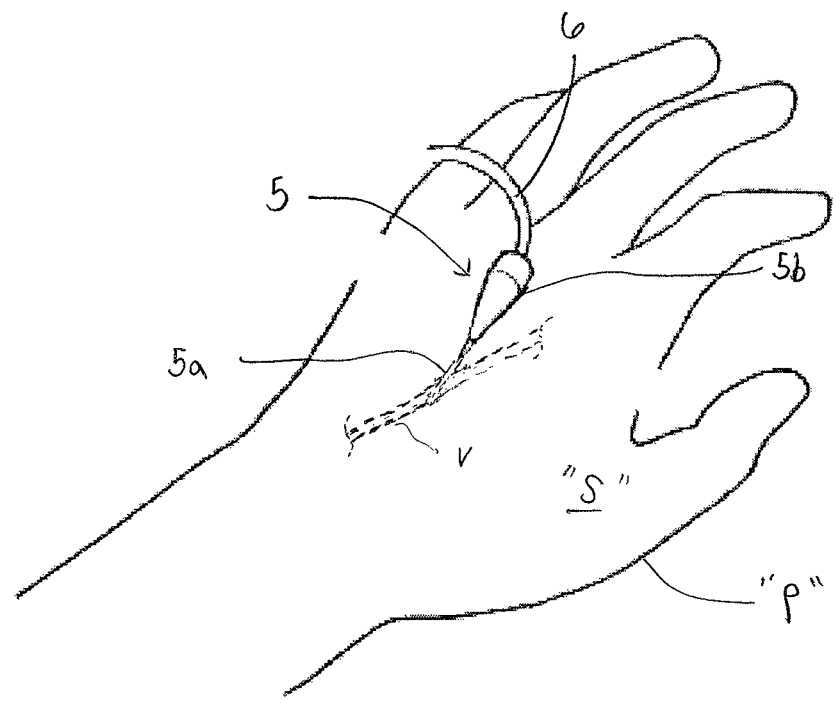
FIG. 2 is an illustration of a hand including a catheter received in a vein.
Figure 3:
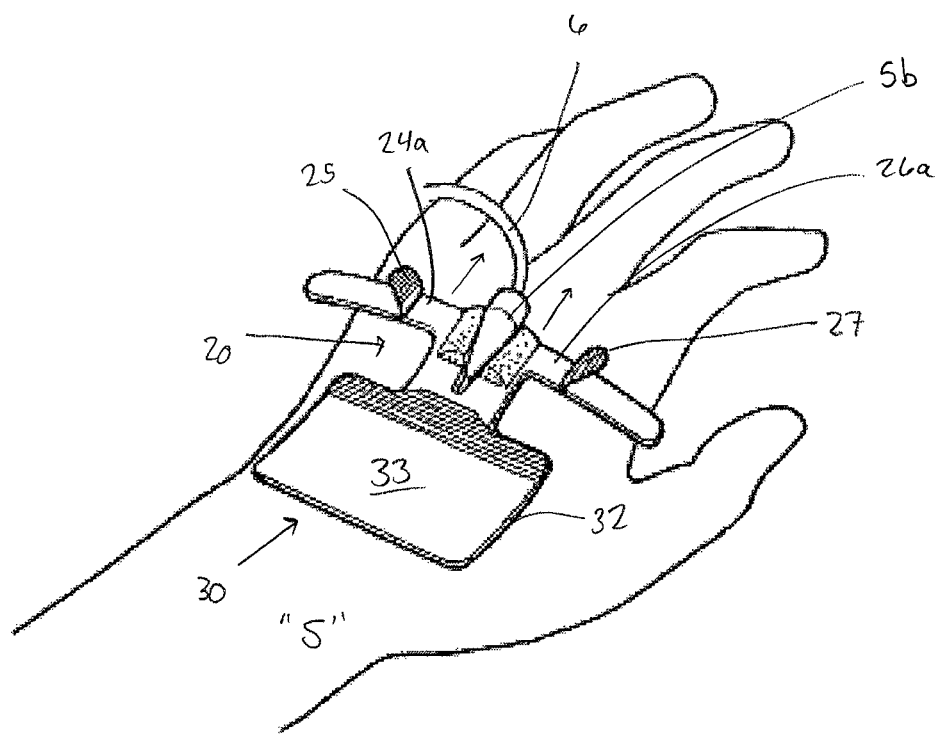
FIG. 3 is a perspective view of the securement device of FIGS. 1A and 1B being positioned about the catheter of FIG. 2.

Still referring to FIGS. 1A and 1B, proximal portion 20 of transparent base 12 defines a substantially V-shaped slot 21 configured to be received about catheter 5 (FIG. 2). Alternatively, slot 21 may be U-shaped, C-shaped or otherwise configured to be received about catheter 5. Extending from top surface 20a of proximal portion 20 about V-shaped slot 21 is a pair of pliable support halves 22a, 22b (collectively, pliable support 22). Pliable support 22 may be constructed of foam, polymer or other suitable flexible material. Pliable support 22 is configured to at least partially enclose hub 5b of catheter 5. As will be discussed in further detail below, pliable support 22 is configured to receive and support an indwelling catheter 5 (FIG. 3). Proximal portion 20 of securement device 10 further includes a pair of securement arms 24, 26. First and second securement arms 24, 26 extend outwardly from V-shaped slot 21 and are of sufficient length and width to be folded over hub portion 5b of catheter 5 when catheter 5 is received in V-shaped slot 21 as will be discussed in further detail below. Securement arms 24, 26 may be of same or different lengths and/or configurations. It is envisioned that proximal portion 20 may include a single or multiple securement arms.

With reference still to FIGS. 1A and 1B, first and second securement arms 24, 26 include respective first and second release layers 25, 27, respectively, for covering adhesive surfaces 24a, 26a (FIG. 3) of respective securement arms 24, 26. Adhesive surfaces 24a, 26a may be coated with adhesive, glue or other suitable material for releasably securing securement arms 24, 26 to the skin of a patient. Release layers 25, 27 protect adhesive surfaces 24a, 26a (FIG. 3) from incidental contact with a care provider, patient or other object until such time as securement arms 24, 26 are ready to be applied. In an alternative embodiment, securement arms 24, 26 may be coated with a substance (not shown) that remains tact-free until moistened or otherwise activated by a clinician. Optionally, bottom surface 20b (FIG. 1B) of proximal portion 20 includes a third release layer 29 selectively covering an adhesive portion (not shown) of proximal portion 20. The adhesive portion may include all or only part of bottom surface 20b of proximal portion 20. As will be discussed in further detail below, bottom surface 20b of proximal portion 20 is configured to adhere to skin "S" of a patient "P" to initially secure securement device 10 to patient "P".

Still referring to FIGS. 1A and 1B, distal portion 30 of transparent base 12 defines a substantially rectangular cover member 32 sized and dimensioned to be folded over proximal portion 20 to further secure first and second securement arms 24, 26 and catheter 5 after securement arms 24, 26 have been secured about catheter 5 to patient "P". Alternative configurations of cover member 32 are envisioned, including circular, triangular and square. Distal portion 30 includes a fourth release layer 33 selectively covering an adhesive portion (not shown) formed on top surface 32a of cover member 32.

The application of securement device 10 will now be described with reference to FIGS. 2-5. Referring initially to FIG. 2, in preparation for using securement device 10, cannula 5a of catheter 5 is inserted into a patient's vein "V" (shown in phantom in FIG. 2) by a clinician (not shown) according to standard practice. Extension tubing set 6 is then connected to hub 5b of catheter 5.

With reference now to FIG. 3, catheter 5 is next held stationary by the clinician as slotted proximal portion 20 of securement device 10 is placed along hub 5b of catheter 5. In the case where bottom surface 20b of proximal portion 20 includes an adhesive portion (not shown), third release layer 29 (FIG. 1B) is removed bottom surface 20b of proximal portion 20 prior to sliding slotted proximal portion 20 about catheter 5. In this manner, proximal portion 20 is at least partially adhered to the skin "S" prior to engagement with first and second securement arms. Catheter 5 is restrained from moving side-to side by pliable support 22.

Figure 4:
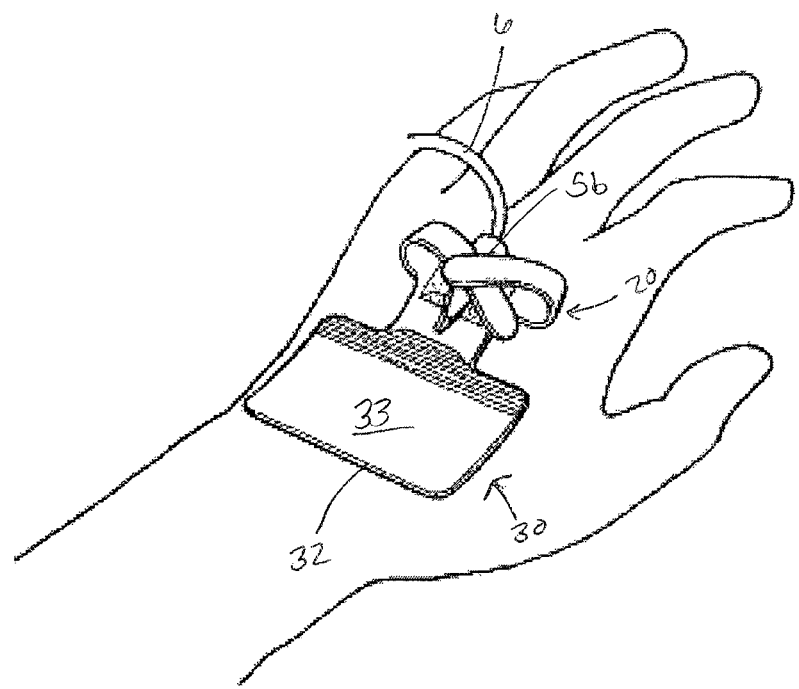
FIG. 4 is a perspective view of the catheter and securement device of FIG. 3, wherein the catheter is partially secured by the securement device.
Figure 5:
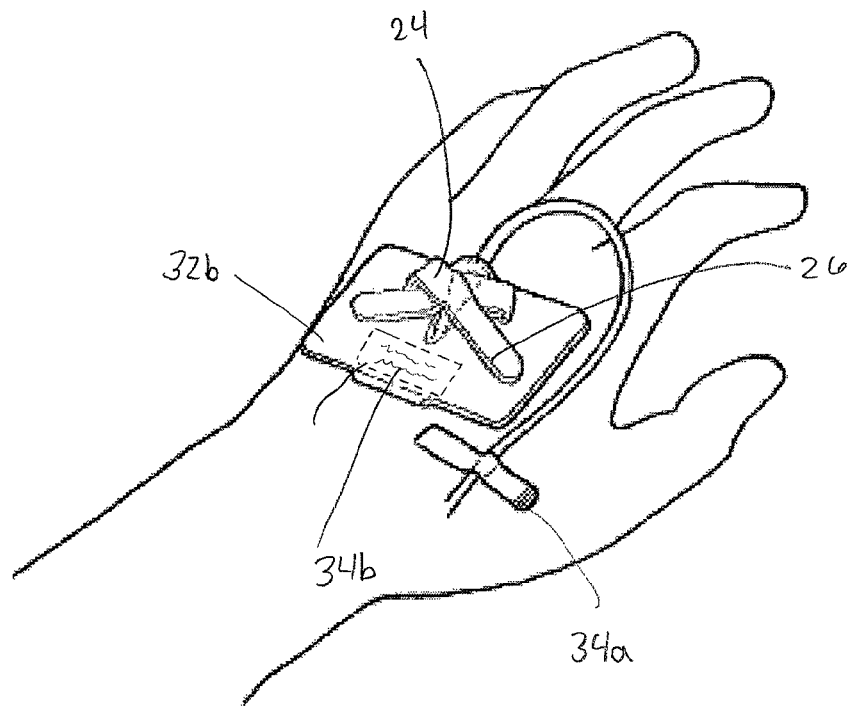
FIG. 5 is a perspective view of the catheter and securement device of FIGS. 3 and 4, wherein the catheter is completely secured by the securement device.

With reference to FIG. 4, once proximal portion 20 of securement device 10 is adhered to skin "S", or at least proximal portion 20 has been positioned about catheter 5 with hub 5b supported by pliable support 22, first release layer 25 on first securement arm 24 is removed to expose adhesive surface 24a. First securement arm 24 is then folded over catheter hub 5b to contain catheter 5 between first and second foam support halves 22a, 22b. Depending on the length of first securement arm 24, first securement arm 24 may be adhered to proximal portion 20 and/or skin "S" of the patient. Second release layer 27 is then removed from second securement arm 26 to expose second adhesive surface 26a. Second securement arm 26 is then folded over catheter hub 5b to adhere second securement arm 26 to first securement arm 24 and catheter hub 5b, and, optionally, adhere second securement arm 26 to proximal portion 20 and/or skin "S".

Next, fourth release layer 33 is removed from top surface 32a of cover member 32 of distal portion 30 to expose the adhesive portion (not shown) formed on top surface 32a of cover member 32. Cover member 32 is then folded to substantially cover hub 5b of catheter 5 and proximal portion 20 of securement device 10 further securing catheter 5 in place. Cover member 32 provides a smooth outer surface for securement device 10. Bottom surface 32b of cover portion 32 may include, for example, a piece of tape 34a and/or label material 34b for taping down the extension tubing and/or recording clinical information. When tubing 6 is taped down, any forces exerted upon tubing 6 "upstream" of catheter 5 will not be transmitted to the injection site.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A securement device comprising:
   a proximal portion including a pliable support and at least one securement arm integrally formed with the proximal portion and extending away from the pliable support, the proximal portion defining a slot extending through the proximal portion from a top surface of the proximal portion to a bottom surface of the proximal portion, the slot configured to receive at least a portion of a catheter, wherein the at least one securement arm is foldable over the portion of a catheter received in the slot to retain the portion of the catheter within the slot; and
   a distal portion including a first adhesive surface configured to be folded over the proximal portion to secure the proximal portion to a patient.

2. The device of claim 1, wherein the at least one securement arm includes a second adhesive surface.

3. The device of claim 2, wherein each of the first and second adhesive surfaces is protected by a release layer.

4. The device of claim 1, wherein the first adhesive surface is protected by a release layer.

5. The device of claim 1, wherein the distal portion is transparent.

6. The device of claim 1, wherein the distal portion defines a substantially rectangular member.

7. The device of claim 1, wherein the proximal portion includes two securement arms.

8. The device of claim 1, wherein the proximal portion includes an adhesive portion on a bottom surface thereof.

9. The device of claim 1, wherein the slot defined by the proximal portion is V-shaped.

10. The device of claim 1, wherein the pliable support is composed of foam.

11. The device of claim 1, wherein in an applied state, the at least one securement arm is folded over the portion of the catheter received within the slot and is positioned between the proximal portion and the distal portion.

12. The device of claim 1, wherein the pliable support comprises a first support half disposed on a first side of the slot and a second support half disposed on a second side of the slot opposite the first side.

13. The device of claim 12, wherein the first support half and the second support half are configured to at least partially enclose a hub of the catheter.

14. The device of claim 1, wherein an end of the at least one securement arm is integrated to the proximal portion at an outside surface of the proximal portion and an opposite end of the at least one securement arm extends away from the pliable support, the opposite end foldable over the portion of a catheter received in the slot to retain the portion of the catheter with the slot.

15. A securement device comprising:
  a proximal portion including a foam support and at least one securement arm integrally formed with the proximal portion and extending away from the foam support, the foam support defining a V-shaped slot from a top surface of the proximal portion through a bottom surface of the proximal portion, the V-shaped slot of the foam support being configured to receive at least a portion of a catheter, wherein the at least one securement arm is foldable over the portion of a catheter received in the V-shaped slot to retain the portion of the catheter in the V-shaped slot; and
  a distal portion including an adhesive surface configured to be folded over the proximal portion to secure the proximal portion to a patient.

16. The device of claim 15, wherein in an applied state, the at least one securement arm is folded over the portion of the catheter received within the slot and is positioned between the proximal portion and the distal portion.

17. The device of claim 15, wherein the slot has a length equal to the length of the proximal portion.

18. A method of securing a catheter to a patient, the method comprising the following steps:
  providing a securement device including a proximal portion and a distal portion, the proximal portion having a pliable support and at least one securement arm integrally formed with the proximal portion, the proximal portion defining a slot extending through the proximal portion from a top surface of the proximal portion to a bottom surface of the proximal portion, the at least one securement arm extending away from the pliable support;
  adhering the proximal portion of the securement device to a patient's skin;
  placing a hub of the catheter within the slot of the proximal portion;
  folding the at least one securement arm over the catheter hub to secure the catheter hub within the slot of the proximal portion;
  engaging the patient's skin with the at least one securement arm to secure the proximal portion to the patient; and
  folding the distal portion over the proximal portion to cover the catheter hub and the proximal portion of the securement device.

19. A securement device comprising:
  a proximal portion including a pliable support and at least one securement arm integrally formed with the proximal portion and extending away from the pliable support, the proximal portion defining a slot extending through the proximal portion from a top surface of the proximal portion to a bottom surface of the proximal portion, the slot configured to receive at least a portion of a catheter, wherein the at least one securement arm is foldable over the portion of a catheter received in the slot to retain the portion of the catheter within the slot, the at least one securement arm being of a length sufficient to engage a patient's skin to secure the proximal portion to the patient; and
  a distal portion including a first adhesive surface configured to be folded over the proximal portion to secure the proximal portion to the patient.

20. A securement device comprising:
  a proximal portion including a foam support and at least one securement arm integrally formed with the proximal portion and extending away from the foam support, the proximal portion defining a V-shaped slot extending through the proximal portion from a top surface of the proximal portion to a bottom surface of the proximal portion, the V-shaped slot configured to receive at least a portion of a catheter, wherein the at least one securement arm is foldable over the portion of a catheter received in the V-shaped slot to retain the portion of the catheter within the V-shaped slot; and
  a distal portion including a first adhesive surface configured to be folded over the proximal portion to secure the proximal portion to a patient.

21. A method of securing a catheter to a patient, the method comprising:
  providing a securement device including a proximal portion and a distal portion, the proximal portion having a foam support and at least one securement arm integrally formed with the proximal portion, the proximal portion defining a V-shaped slot extending through the proximal portion from a top surface of the proximal portion to a bottom surface of the proximal portion, the at least one securement arm extending away from the foam support;
  adhering the proximal portion of the securement device to a patient's skin;
  placing a hub of the catheter within the V-shaped slot of the proximal portion;
  folding the at least one securement arm over the catheter hub to secure the catheter hub within the V-shaped slot of the proximal portion;
  engaging the patient's skin with the at least one securement arm to secure the proximal portion to the patient; and
  folding the distal portion over the proximal portion to cover the catheter hub and the proximal portion of the securement device.

22. A securement device comprising:
  a proximal portion including a foam support and at least one securement arm integrally formed with the proximal portion and extending away from the foam support, the proximal portion defining a V-shaped slot extending through the proximal portion from a top surface of the proximal portion to a bottom surface of the proximal portion, the V-shaped slot configured to receive at least a portion of a catheter, wherein the at least one securement arm is foldable over the portion of a catheter received in the V-shaped slot to retain the portion of the catheter within the V-shaped slot, the at least one securement arm being of a length sufficient to engage a patient's skin to secure the proximal portion to the patient; and
  a distal portion including a first adhesive surface configured to be folded over the proximal portion to secure the proximal portion to the patient.

* * * * *